US011701397B2

(12) United States Patent
Garcia-Rodenas et al.

(10) Patent No.: US 11,701,397 B2
(45) **Date of Patent: *Jul. 18, 2023**

(54) **USE OF *L. REUTERI* FOR RECOVERY OF MICROBIOTA DYSBIOSIS IN EARLY LIFE**

(71) Applicant: BIOGAIA AB, Stockholm (SE)

(72) Inventors: Clara Lucia Garcia-Rodenas, Forel (CH); Bernard Berger, Maracon (CH); Catherine Ngom-Bru, Montpreveyres (CH); Melissa Lepage, Savigny (CH); Tara Neville, Geneva (CH)

(73) Assignee: BIOGAIA AB, Stockholm (SE)

( * ) Notice: Subject to any disclaimer, the term of this patent is extended or adjusted under 35 U.S.C. 154(b) by 0 days.

This patent is subject to a terminal disclaimer.

(21) Appl. No.: 17/749,694

(22) Filed: May 20, 2022

(65) Prior Publication Data

US 2022/0331380 A1 Oct. 20, 2022

Related U.S. Application Data

(63) Continuation of application No. 15/521,977, filed as application No. PCT/EP2015/075164 on Oct. 29, 2015, now Pat. No. 11,369,646.

(30) Foreign Application Priority Data

Oct. 29, 2014 (EP) .................................... 14190941

(51) Int. Cl.

| | |
|---|---|
| ***A61K 35/747*** | (2015.01) |
| ***A23L 33/00*** | (2016.01) |
| ***A23L 33/135*** | (2016.01) |
| ***A61K 35/745*** | (2015.01) |
| ***A61K 31/702*** | (2006.01) |
| ***A61K 31/733*** | (2006.01) |
| ***A61K 45/06*** | (2006.01) |
| ***A61K 9/00*** | (2006.01) |

(52) U.S. Cl.

CPC .......... *A61K 35/747* (2013.01); *A23L 33/135* (2016.08); *A23L 33/40* (2016.08); *A61K 9/0053* (2013.01); *A61K 31/702* (2013.01); *A61K 31/733* (2013.01); *A61K 35/745* (2013.01); *A61K 45/06* (2013.01); *A23V 2002/00* (2013.01); *A23Y 2220/71* (2013.01)

(58) Field of Classification Search

None

See application file for complete search history.

(56) References Cited

U.S. PATENT DOCUMENTS

| | | | |
|---|---|---|---|
| 2011/0129452 | A1 | 6/2011 | Rochat et al. |
| 2017/0216375 | A1 | 8/2017 | Mollstam et al. |

FOREIGN PATENT DOCUMENTS

| | | |
|---|---|---|
| EP | 1974743 | 10/2008 |
| EP | 2127661 | 12/2009 |
| EP | 2609813 | 7/2013 |

OTHER PUBLICATIONS

Abrahamsson et al. “Probiotic Lactobacilli in Breast Milk and Infant Stool in Relation to Oral Intake During the First Year of Life” Journal of Pediatric Gastroenterology and Nutrition, 2009, vol. 49, pp. 349-354.

Vaarala, Outi, Mark A. Atkinson, and Josef Neu. “The “perfect storm” for type 1 diabetes: the complex interplay between intestinal microbiota, gut permeability, and mucosal immunity.” Diabetes 57.10 (2008): 2555-2562. (Year: 2008).

Matamoros, Sebastien, et al. “Development of intestinal microbiota in infants and its impact on health.” Trends in microbiology 21.4 (2013): 167-173. (Year: 2013).

Morrow, Ardythe L., et al. “Early microbial and metabolomic signatures predict later onset of necrotizing enterocolitis in preterm infants.” Microbiome 1.1 (2013): 1-16. (Year: 2013).

Werner, Erika F., et al. “Health outcomes for vaginal compared with cesarean delivery of appropriately grown preterm neonates.” Obstetrics and gynecology 121.6 (2013): 1195.

Oneel, Mehmet Yekta, et al. “Lactobacillus reuteri for the prevention of necrotising enterocolitis in very low birthweight infants: a randomised controlled trial.” Archives of Disease in Childhood-Fetal and Neonatal Edition 99.2 (2014): F110-F115.

Kuang, Ya-Shu, et al. “Composition of gut microbiota in infants in China and global comparison.” Scientific reports 6 (2016): 36666. (Year: 2016).

Azad, Meghan B., et al. “Gut microbiota of healthy Canadian infants: profiles by mode of delivery and infant diet at 4 months.” Cmaj 185.5 (2013): 385-394. (Year: 2013).

*Primary Examiner* — Robert J Yamasaki

(74) *Attorney, Agent, or Firm* — K&L Gates LLP

(57) ABSTRACT

The invention concerns *Lactobacillus reuteri* for use in the prevention or treatment of microbiota dysbiosis, in particular, decreased levels of Actinobacteria and increased levels of Proteobacteria, in young mammals and in the prevention or treatment of disorders associated therewith. The microbiota dysbiosis may have been cause by numerous factors including being born by caesarean section, exposure to antibiotics in utero or after birth, or, parenteral feeding, hospitalizing, psychological stress or by gastrointestinal dysfunctions. The disorders that may be treated or prevented by preventing or treating microbiota dysbiosis include propensity to infection, allergy, type I diabetes mellitus, insulin resistance, type 2 diabetes, celiac disease, peripheral and central adiposity, obesity, necrotizing enterocolitis, inflammatory bowel disease, such as Crohn’s disease and ulcerative colitis, and functional gastrointestinal disorders such as IBS, functional diarrhea, functional constipation, recurrent abdominal pain, and dyspepsia.

15 Claims, 2 Drawing Sheets

USE OF *L. REUTERI* FOR RECOVERY OF MICROBIOTA DYSBIOSIS IN EARLY LIFE

CROSS REFERENCE TO RELATED APPLICATIONS

The present application is a continuation of U.S. patent application Ser. No. 15/521,977, filed on Apr. 26, 2017, which is a National Stage of International Application No. PCT/EP2015/075164, filed on Oct. 29, 2015, which claims priority to European Patent Application No. 14190941.6, filed on Oct. 29, 2014, the entire contents of which are being incorporated herein by reference.

FIELD OF THE INVENTION

The present invention relates generally to the field of infant health, in particular microbial colonization in the intestine of young mammals. The invention specifically relates to administration of *L. reuteri* to young mammals up to the age of three years in humans, and the equivalent age in animals, for promoting the recovery of microbiota dysbiosis. The invention also relates to the prevention or treatment of disorders associated with microbiota dysbiosis.

BACKGROUND

The present invention applies to all mammals, including animals and humans. Microbial colonisation of the infant intestine is a key triggering factor for the development of the infant gut and immune system. Immediately before birth, the gastro-intestinal tract of a baby is thought to be virtually sterile. During the normal process of birth, it encounters bacteria from the vagina, digestive tract and skin of the mother and starts to become colonised. The fecal microbiota of a healthy, vaginally-delivered, breast-fed infant of age 2 to 6 months is generally dominated by Bifidobacteria species with some *Lactobacillus* species and much lesser amounts of other bacteria groups such as *Bacteroides*, and Proteobacteria, including the potentially pathogenic genera such as *Escherichia, Shigella* and *Klebsiella*. In the healthy, vaginally-delivered, breast-fed infant, Bifidobacteria form the basis of the microbiota accounting for 30-50% of total bacteria in the infant gut.

This may be taken to represent the optimum microbiota for this age group, keeping in mind, however, that geographical factors influence largely the microbiota. Thus, the microbiota of a healthy vaginally-delivered, breast-fed infant of age 2 to 6 months born in one part of the world for example, may be different to that in another.

In any case, after the completion of weaning at about 2-3 years of age, a pattern of gut microbiota that resembles the adult pattern becomes established.

Microbiota dysbiosis may be defined as a significant deviation from a balanced microbiota, in terms of global microbiota profile, metabolism or levels of particular taxa. Microbiota dysbiosis is usually associated with and increased vulnerability to disease. For example, reduced levels of *Bifidobacterium* are associated with increased risk of infection and other pathologies in infants.

A growing body of evidence indicates that the mode of delivery impacts considerably this colonization process. During vaginal delivery, microbiota from the mother's vagina and gut provides the bacteria that initiate intestinal colonization in the infant. By contrast, during caesarean section (C-section), there is no direct contact with the mother fecal and vaginal microbiota, and the initial colonizers are essentially environmental bacteria. Consequently, C-section babies have substantially different founding microbiota composition and a delayed microbiota colonization compared to vaginally delivered babies. C-section microbiota is characterized by alterations in bacterial diversity, reduced abundance of *Bifidobacterium* spp. and *Bacteroides* spp. and increased levels of *C. difficile* [Adlerberth, I., (2009), AE Wold Establishment of the gut microbiota in Western infants, Acta Pœdiatrica, 98, 229-238]. Microbiota alterations can be durable and have been detected several years after birth [Salminen, S., Gibson, G. R., McCartney, A. L. and Isolauri, E. (2004), Influence of mode of delivery on gut microbiota composition in seven year old children, Gut, 53, 1388-1389]. Increased levels of the phylum Proteobacteria, including potentially pathogenic genera such as *Escherichia, Shigella* and *Klebsiella*, are also observed in infants born by C-section.

Caesarean delivery rates are increasing world-wide and currently represent more than 30% of births in very populated countries (e.g. U.S.A., China, Brazil).

Microbiota dysbiosis may be induced by events other than C-section delivery including premature birth, exposure to antibiotics in utero, during delivery or after birth, parenteral feeding, hospitalization, or psychological stress. Microbiota dysbiosis may also result from gastrointestinal dysfunctions (digestive disorders, motility disorders, gastrointestinal reflux, slow gastrointestinal transit, oral feeding intolerance, constipation, diarrhea), Hirschsprung's disease, short bowel syndrome, gastrointestinal infection and inflammation affecting the gastrointestinal tract (such as Necrotisis enterocolitis) and obstruction pathologies.

Thus, young mammals, in particular, infants who have suffered any of these events are at risk of microbiota dysbiosis (aberrant microbiota colonization).

It is believed that aberrant microbiota colonization can explain the increased occurrence of certain disorders in those individuals born by C-section.

These disorders include severe and/or highly prevalent conditions such as infection, allergy, type I diabetes mellitus [Neu, J., Rushing, J. (2011), Caesarean versus Vaginal Delivery: Long term infant outcomes and the Hygiene Hypothesis, *Clin. Perinatol.,* 38, 321-331], celiac disease, peripheral and central adiposity [Mesquita, (2013)] or obesity [HAS Goldani, HAS, Bettiol H., Barbieri M. A. et al. (2011), Caesarean delivery is associated with an increased risk of obesity in adulthood in a Brazilian birth cohort study, *Am. J. Clin. Nutr.,* 93,1344-7] that significantly impair the quality of life of the individual and also result in a considerably social and health care cost.

The risk of having these disorders is increased in those who have suffered microbiota dysbiosis, whatever the cause of the dysbiosis. Thus, individuals who were born prematurely (either vaginally or by C-section), who were exposed to antibiotics in utero, during delivery or after birth, or who were fed parenterally, who have suffered from gastrointestinal dysfunctions (digestive disorders, motility disorders, gastrointestinal reflux, slow gastrointestinal transit, oral feeding intolerance), Hirschsprung's disease, inflammation affecting the gastrointestinal tract (such as Necrotizing enterocolitis) and obstruction pathologies in the three first years of life are also at risk of having the above mentioned disorders.

On the other hand, as well as being a consequence of gastrointestinal disorders, microbiota dysbiosis may actually cause them. Thus, microbiota dysbiosis may result in, for example, digestive disorders, motility disorders, gastrointestinal reflux, slow gastrointestinal transit, oral feeding intolerance, Hirschsprung's disease, and inflammation affecting the gastrointestinal tract (such as Necrotizing enterocolitis) and obstruction pathologies.

Thus, preventing and treating microbiota dysbiosis occurring early in life (for example, up to the age of three) may prevent or treat the numerous disorders associated therewith, whether those disorders occur in infancy, or later in life.

The treatment of microbiota dysbiosis, includes re-establishing a microbiota not significantly different from that observed healthy young mammals, who are not experiencing microbiota dysbiosis. This means that the various bacterial populations are re-established in their optimal relative abundance.

Pre- and probiotics have been proposed as a means to improve the microbiota composition in C-section babies. However, up until now, there are no published data demonstrating the capacity of probiotic to re-establish a healthy, balanced microbiota—one where the various gut bacteria are present in the optimal relative abundance.

The effect of the administration of *L. reuteri* to mothers with a family history of atopic disease during the last 4 weeks of pregnancy and to their babies from birth until 12 months has been described. While the probiotic treatment resulted in a higher prevalence of *L. reuteri* in the stool samples from infants in the active as compared to the placebo treated group, during the first year of life, interestingly, the administration of *L. reuteri* did not affect bifidobacteria or *C. difficile* colonization [Abrahamsson et al (2009) Probiotic Lactobacilli in Breast milk and infant stool in relation to oral intake during the first year of life, *J. Ped. Gastroenterology and Nutrition* 49, pp 1-6].

In international patent application WO2008116892, it is described how the administration of *Bifidobacterium lactis* CNCM 1-3446 to mice in an animal model of C-section led to an increase in levels of *Bifidobacterium breve*, but had no effect on levels of Bifidobacterimum *longum*.

In WO2010/010021 it was demonstrated that infants born by C-section have lower levels of fecal IgA compared to vaginally delivered infants. Administration of infant formula containing *Bifidobacterium longum* increased levels of fecal IgA in the C-section infants. The microbiota of the infants was not studied.

There is a need to prevent disorders associated with microbiota dysbiosis, including propensity to infection, allergy, type I diabetes mellitus, insulin resistance, type 2 diabetes, celiac disease, peripheral and central adiposity, obesity, necrotizing enterocolitis, inflammatory bowel disease, such as Crohn's disease and ulcerative colitis, and functional gastrointestinal disorders such as IBS, functional diarrhea, functional constipation, recurrent abdominal pain and dyspepsia.

SUMMARY

The invention concerns *Lactobacillus reuteri* for use in the prevention or treatment of microbiota dysbiosis in a young mammal at risk of or suffering from microbiota dysbiosis.

According to one aspect of the invention, the administration of *L. reuteri* increases or maintains levels of Actinobacteria and/or decreases or maintains levels of Proteobacteria so that these levels are not significantly different from those in young mammals not suffering from microbiota dysbiosis.

The treatment generally for young mammals aged up to approximately three years of age in humans and the equivalent age in animals.

The invention also concerns the use of *Lactobacillus reuteri* for preventing or treating disorders associated with said microbiota dysbiosis. The disorders may occur when the mammal is young, for example under the age of three for a human and the equivalent age for an animal) or, they may occur later in life of the mammal.

The young mammal at risk of or suffering from microbiota dysbiosis may have been born or will be by caesarean section, been or is being exposed to antibiotics in utero, during delivery or after birth, or, been or is being fed parenterally. The young mammal at risk of or suffering from microbiota dysbiosis may be or may have been hospitalized, suffering from psychological stress or from gastrointestinal dysfunctions including digestive disorders, motility disorders, gastrointestinal reflux, slow gastrointestinal transit, oral feeding intolerance, constipation, diarrhea, Hirschsprung's disease, short bowel syndrome, gastrointestinal infection and inflammation affecting the gastrointestinal tract, such as Necrotizing enterocolitis, and obstruction pathologies.

The disorders that may be treated or prevented by preventing or treating microbiota dysbiosis include propensity to infection, allergy, type I diabetes mellitus, insulin resistance, type 2 diabetes, celiac disease, peripheral and central adiposity, obesity, necrotizing enterocolitis, inflammatory bowel disease, such as Crohn's disease and ulcerative colitis, and functional gastrointestinal disorders such as IBS, functional diarrhea, functional constipation, recurrent abdominal pain, and dyspepsia.

The young mammal to be treated may be animal, or a human foetus, pre-term or term-born infant or a toddler.

The *Lactobacillus reuteri* may be administered to the foetus via the expectant mother or may be administered to the young mammal directly or indirectly, via the lactating mother.

The administration period for the foetus is generally at least one week, preferably two weeks, more preferably at least one month and even more preferably for the entirety of the gestation period. The administration period for the young mammal is generally at least 4 weeks, preferably 2-36 months in humans and the equivalent age in animals.

The *Lactobacillus reuteri* may be administered directly to the infant or toddler in its pure form, or diluted in water or breast milk, in a food supplement, or in a milk fortifier, or in any milk support used during trophic feeding, or in a growing-up milk, or in a milk based drink or in an infant formula, such as a formula for premature infants, a starter formula or a follow-on formula, in a pharmaceutical or neutriceutical composition, a growing-up milk, a milk-based drink, a food supplement, in a baby food, in an enteral nutritional product, a milk-based yoghurt, a dessert or pudding, in a biscuit, or cereal bar, cereal or, in a fruit-based drink.

The *Lactobacillus reuteri* may be administered to the expectant or lactating mother orally, preferably in foods, drinks, dietary supplements or pharmaceutical compositions.

The *Lactobacillus reuteri* may be administered to infant or toddler as a daily dose of from $1\times10^3$ to $1\times10^{12}$, preferably, $1\times10^7$ to $1\times10^{11}$ cfu (cfu=colony forming unit).

The *Lactobacillus reuteri* may be administered to the expectant or lactating mother, or infant as a composition comprising between $1\times10^3$ and $1\times10^{12}$ cfu/g of dry composition. Said composition may comprise further ingredients or prebiotics, preferably selected from inulin, fructo-oligosaccharide (FOS), short-chain fructo-oligosaccharide (short chain FOS), galacto-oligosaccharide (GOS), fucosylated oligosaccharides, Sialylated oligosaccharides, human milk oligosaccharides (HMO) and cow milk oligosaccharides (CMOS).

Said composition may comprise one or more additional probiotics, preferably selected from *Bifidobacterium longum* BB536 (ATCC BAA-999); *Lactobacillus rhamnosus* (CGMCC 1.3724), *Bifidobacterium lactis* (NCC2818) or mixtures thereof.

The *Lactobacillus reuteri* may be alive, inactivated or dead, fragmented, or in the form of fermentation products or metabolites, or a mixture of any or all of these states.

Preferably, the *Lactobacillus reuteri* is *Lactobacillus reuteri* DSM 17938.

The administration of the *L. reuteri* may be to a foetus via the mother. It may also be to a pre-term or term-born infant either directly or via mothers' milk.

DETAILED DESCRIPTION

Figure 1:
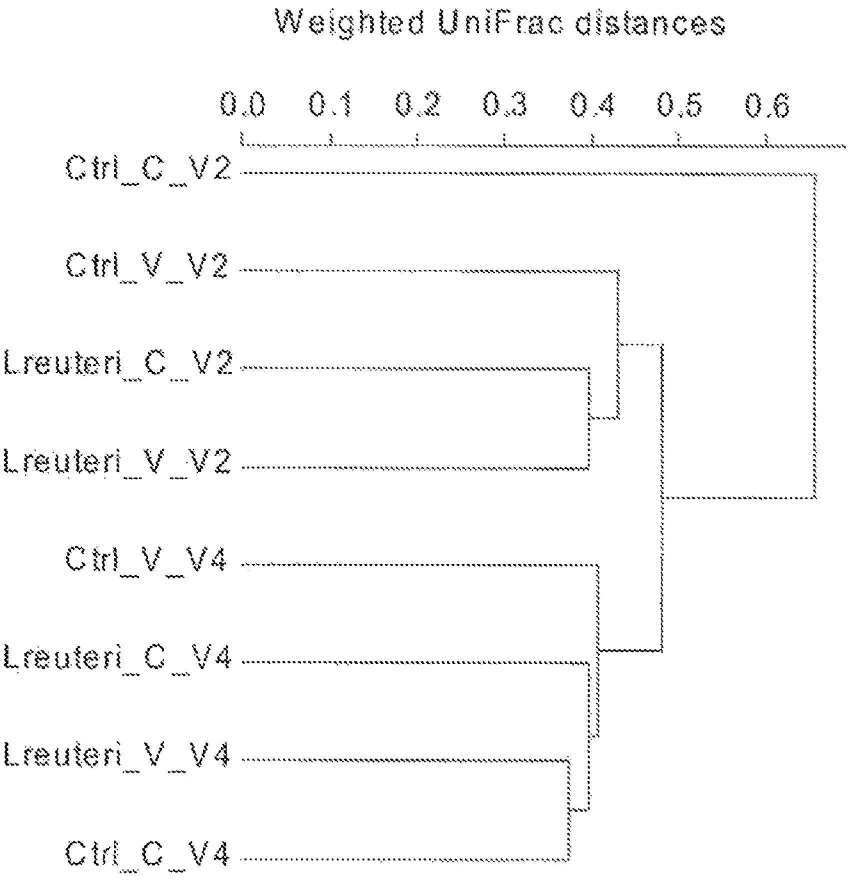
FIG. 1: Hierarchical clustering carried out on the mean weighted UniFrac distance matrix (i.e. UniFrac distances measuring the phylogenetic dissimilarity of the microbiota composition) of the 4 groups—Vaginal (V) and Caesarian (C) subjects fed Control (Ctrl) or *L. reuteri* formula (*L. reuteri*)—at the two ages—14 days (V2) and 4 month (V4). In this dendogram, the groups are joined together in a hierarchical way from the closest, that is the most phylogenetically similar, to the furthest apart, that is the most different.
Figure 2A:
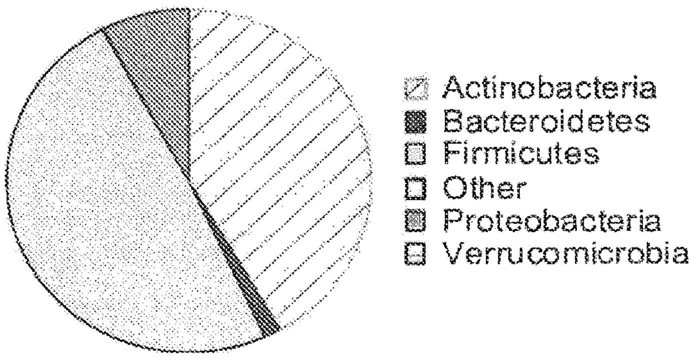
FIG. 2: Relative abundance of Phylum taxa in feces of each experimental group at 2 weeks. Control Vaginal (A), Control Cesarian (B), *L. reuteri* Vaginal (C), and *L. reuteri* Cesarian (D). Taxa that have a significantly different relative abundance are labeled in bold if more abundant compared to Control Vaginal group, or in bold and italic if less abundant than in Control Vaginal group.
Figure 2B:
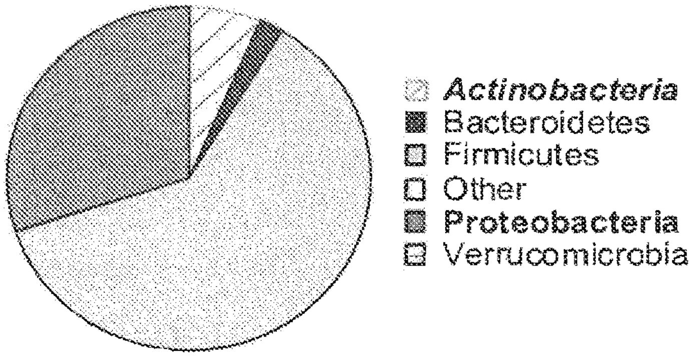
Figure 2C:
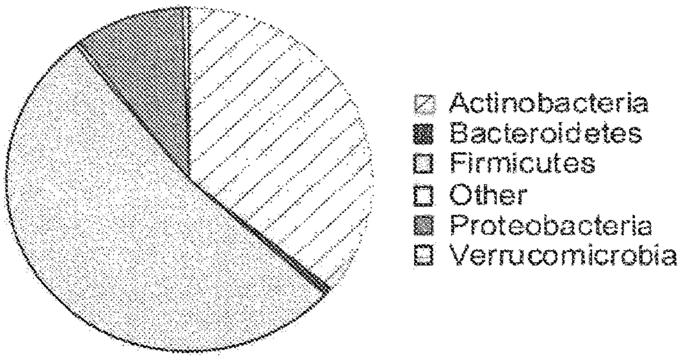
Figure 2D:
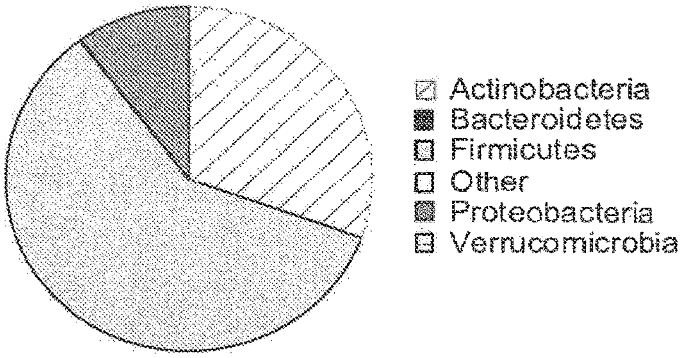

Definitions:

In this specification, the following terms have the following meanings:

"Infants": according to the Commission Directive 2006/141/EC of 22 Dec. 2006 on infant formulae and follow-on formulae, article 1.2 (a), the term "infants" means children under the age of 12 months.

"Pre-term infant" generally means an infant born before 37 weeks gestation. "Term Born Infant" generally means an infant born after 37 weeks gestation. "Toddler" generally means a child from when he can walk up to three years old.

"Young mammal" means in the context of the present invention a mammal who has not entered puberty. This corresponds to infancy and childhood in humans and the equivalent age in animals.

"Probiotic" means microbial cell preparations or components or metabolites of microbial cells with a beneficial effect on the health or well-being of the host [Salminen, S. et al. (1999); Probiotics: how should they be defined, *Trends Food Sci. Technol.,* 10 107-10]. The definition of probiotic is generally admitted and in line with the WHO definition. The probiotic can comprise a unique strain of micro-organism, a mix of various strains and/or a mix of various bacterial species and genera. In case of mixtures, the singular term "probiotic" can still be used to designate the probiotic mixture or preparation. For the purpose of the present invention, micro-organisms of the genus *Lactobacillus* are considered as probiotics.

"Prebiotic" generally means a non-digestible food ingredient that beneficially affects the host by selectively stimulating the growth and/or activity of micro-organisms present in the gut of the host, and thus attempts to improve host health.

"Allergy" means an allergy which has been detected by a medical doctor and which can be treated occasionally or in a more durable manner. A "food allergy" is an allergy with respect to a food constituent.

"Infant formulae": according to the Commission Directives 2006/141/EC of 22 Dec. 2006 and/or 91/321/EEC of 14 May 1991 on infant formulae and follow-on formulae, article 1.2 (c), the term "infant formulae" means foodstuffs intended for particular nutritional use by infants during the first four to six months of life and satisfying by themselves the nutritional requirements of this category of persons. It has to be understood that infants can be fed solely with infant formulas, or that the infant formula can be used by the carer as a complement of human milk. It is synonymous to the widely used expression "starter formula".

"Follow-on formulae": according to the Commission Directives 2006/141/EC of 22 Dec. 2006 and/or 91/321/EEC of 14 May 1991 on infant formulae and follow-on formulae, article 1.2 (d), the term "follow-on formulae" means foodstuffs intended for particular nutritional use by infants aged over four months and constituting the principal liquid element in a progressively diversified diet of this category of persons.

"Growing-up milk": milk-based nutritional composition especially adapted to a child of between one year and three years old.

"Human Milk fortifier": Nutritional composition for infants or young children intended to be added to or diluted with human milk.

The term "hypoallergenic composition" means a composition which is unlikely to cause allergic reactions.

The term "sialylated oligosaccharide" means an oligosaccharide having a sialic acid residue.

The term "fucosylated oligosaccharide" means an oligosaccharide having a fucose residue.

All percentages are by weight unless otherwise stated.

As used in this specification, the words "comprises", "comprising", and similar words, are not to be interpreted in an exclusive or exhaustive sense. In other words, they are intended to mean "including, but not limited to".

Any reference to prior art documents in this specification is not to be considered an admission that such prior art is widely known or forms part of the common general knowledge in the field.

The inventors have demonstrated that administration of *L. reuteri* to young mammals, generally up to the age of three in humans and the equivalent age in mammals prevents microbiota dysbiosis.

The administration of *L. reuteri* thus prevents disorders associated with microbiota dysbiosis. These disorders include propensity to infection, allergy, type I diabetes mellitus, insulin resistance, type 2 diabetes, celiac disease, peripheral and central adiposity, obesity, necrotizing enterocolitis, inflammatory bowel disease, such as Crohn's disease and ulcerative colitis, and functional gastrointestinal disorders such as IBS, functional diarrhea, functional constipation, recurrent abdominal pain, and dyspepsia.

Microbiota dysbiosis may be induced by C-section delivery, premature birth, exposure to antibiotics in utero or after birth, parenteral feeding, hospitalization, or psychological stress, gastrointestinal dysfunctions (digestive disorders, motility disorders, gastrointestinal reflux, slow gastrointestinal transit, oral feeding intolerance, constipation, diarrhea), Hirschsprung's disease, short bowel syndrome, gastrointestinal infection and inflammation affecting the gastrointestinal tract (such as Necrotisis enterocolitis) and obstruction pathologies.

Thus, administration of *L. reuteri* will especially benefit individuals who are experiencing/have experienced at least one of these events.

According to a preferred embodiment of the invention, administration of *L. reuteri* prevents or treats microbiota dysbiosis and disorders associated therewith in infants who have been delivered by C-section.

According to further embodiments of the invention the *L. reuteri* is administered to young mammal, who has been exposed to antibiotics in utero or after birth, or who has been fed parenterally for the prevention or treatment of microbiota dysbiosis and the disorders associated therewith.

Young mammals, in particular infants who have suffered microbiota dysbiosis at birth, or in the months, or in the first three years after birth because of any of the events mentions previously may go on to manifest any of the above mentioned disorders in the weeks or months or even years after the microbiota dysbiosis first occurred. Thus, treatment with *L. reuteri* before birth (prenatally) or in the first three years of life in a human and the equivalent time in an animal prevents or treats disorders that:

(a) may occur in the first three years of life in humans (or the equivalent age in animals) and (b) may occur later in life (for example, up to the adulthood), but which were initially caused by microbiota dysbiosis at birth and/or in the three years after birth.

Examples of disorders that manifest themselves later in life are poor resistance to infection, allergy, asthma, atopic disease, type I diabetes mellitus, insulin resistance, type 2 diabetes, celiac disease, peripheral and central adiposity, and obesity, necrotizing enterocolitis, and inflammatory bowel disorder/or disease.

While, generally, some of the causes of microbiota dysbiosis may occur at any time of life of an individual, the current invention focuses on treatment of the young mammal up to the age of three years in humans, and the equivalent age for animals. The gut and the immune system develops during this period and is modulated by the composition of the microbiota colonizing the gut. Thus, preventing and treating microbiota dysbiosis during this critical time has a positive outcome for individuals during and past early childhood and reaching into adulthood.

According to several embodiments of the invention, administration of *L. reuteri* to humans of up to three years of age, or to animals of the equivalent age, who are suffering from, or at risk of suffering from microbiota dysbiosis, prevents or treats disorders associated with microbiota dysbiosis.

According to one embodiment of the invention, the disorder associated with microbiota dysbiosis to be prevented or treated is poor resistance to infection.

According to another embodiment of the invention, the disorder associated with microbiota dysbiosis to be prevented or treated is peripheral and central adiposity, and/or obesity.

According to another embodiment of the invention, the disorders associated with microbiota dysbiosis to be prevented or treated are type I diabetes mellitus, insulin resistance, or type 2 diabetes.

According to another embodiment of the invention, the disorders associated with microbiota dysbiosis to be prevented or treated are inflammatory bowel disease or necrotizing enterocolitis.

According to another embodiment of the invention, the disorders associated with microbiota dysbiosis to be prevented or treated allergy, asthma, and/or atopic disease.

For all of the above mentioned embodiments, the microbiota dysbiosis, and thus, the ensuing disorder, may have been induced by any one or more of C-section delivery, premature birth (vaginally or by C-section), exposure to antibiotics in utero or after birth, parenteral feeding in the first three years of life, hospitalization, or psychological stress, gastrointestinal dysfunctions (digestive disorders, motility disorders, gastrointestinal reflux, slow gastrointestinal transit, oral feeding intolerance, constipation, diarrhea), Hirschsprung's disease, short bowel syndrome, gastrointestinal infection and inflammation affecting the gastrointestinal tract (such as Necrotisis enterocolitis) and obstruction pathologies.

According to a preferred embodiment of the invention, the administration of *L. reuteri* is to infants and toddlers who have been delivered by C-section.

Any strain of *L. reuteri* may be used according to the invention. According to a preferred embodiment the *L. reuteri* is *Lactobacillus reuteri* DSM 17938, the *L. reuteri* strain owned by Biogaia AB, Sweden, having the scientific strain designation DSM 17938, formerly *L. reuteri* ATCC 55730. The DSM identification refers to the DSMZ Deutsche Sammlung von Mikroorganismen und Zellkulturen GmbH Inhoffenstr. 7b, D-38124 Braunschweig, Germany. DSM 17938. Deutsche Sammlung von Mikroorganismen und Zellkulturen GmbH Inhoffenstr. 7b D-38124 Braunschweig—Germany.

Other examples of *L. reuteri* suitable for use according to the invention *L. reuteri* are ATCC PTA 6475, *L. reuteri* ATCC PTA 4659 and *L. reuteri* ATCC PTA 5289 (available from Biogaia, Sweden), *L. reuteri* RC-14 (sold by Christian Hansen, France), *L. reuteri* NCIMB 30242 (sold as supplement called Cardioviva, by Micropharma Ltd., Canada) and *L. reuteri* DSMZ 17648 (sold under the commercial name Pylopass, by Lonza, Switzerland)

The administration of the *L. reuteri* may be to a foetus, via the mother. It may also be to a pre-term or term-born infant, either directly or via mothers' milk. The administration is generally up to the age of three years old, or the equivalent age in an animal.

Doses of Probiotic:

The probiotic may be administered as a daily dose and in the form of a composition. The daily dose of *L. reuteri* administered to the expectant or breast feeding mother is from $1\times10^6$ to $1\times10^{12}$ cfu, preferably $1\times10^8$ to $1\times10^{11}$ cfu (cfu=colony forming unit). The daily dose, suitable for newborn babies, ranges from $1\times10^3$ to $1\times10^{12}$, preferably, $1\times10^7$ to $1\times10^{11}$ cfu.

Thus, *L. reuteri* may be present in the composition in a wide range of percentages provided that it delivers the beneficial effect described. However, preferably, the *L. reuteri* is present in the composition in an amount equivalent to between $1\times10^3$ and $1\times10^{12}$ cfu/g of dry composition. Preferably, for administration to the expectant or lactating mother or the young adult, the probiotic is present in an amount equivalent to between $1\times10^4$ to $1\times10^{11}$ cfu/g of dry composition. The amount of probiotic present per gram of dry composition for administration to the neonates, toddlers and children may be lower, preferably, $1\times10^6$ to $1\times10^9$, and, of course, the daily doses described above should be respected.

The above doses include the possibilities that the bacteria are live, inactivated or dead, or even present as fragments such as DNA or cell wall or cytoplasmic materials, or as bacteria fermentation products or as bacteria metabolites. In other words, the quantity of bacteria which the formula contains is expressed in terms of the colony forming ability of that quantity of bacteria as if all the bacteria were live, irrespective of whether they are, in fact, live, inactivated or dead, fragmented, or in the form of fermentation products or metabolites, or a mixture of any or all of these states.

Method of Administration (i) Administration to Expectant Mothers:

The *L. reuteri* can be administered to the expectant mothers by various ways as long as it induces a contact with gastro-intestinal tract or vagina of the expectant mothers. For example, *L. reuteri* may be administered vaginally as a capsule, suppository or tablet. Preferably, the administration is oral. Preferably, *L. reuteri* is orally administered in a composition as part of the food, drinks, tablets, capsules, pastilles or chewing gum, or dietary supplements of the expectant mothers. The composition can also be administered in a pharmaceutical composition. However, in pathological conditions or when enteral feeding is otherwise used, the administration of the composition can be added to the enteral feeding composition. The enteral feeding may be nasogastric, nasojejunal, or via a percutaneous endoscopic gastrostomy, or jejunostomy.

(ii) Administration to Newborn Mammals:

alone (pure or diluted in water or mother's milk for example) as a supplement (for example as a human milk fortifier supplement), or as a pharmaceutical or nutraceutical composition, or as an ingredient in an infant milk formula. Such a formula may be an infant "preterm formula" if the young mammal is born before term or has a low birth weight, a "starter formula" or a "follow-on formula". A follow on formula is generally given to an infant of older than six months. The formula may also be an hypoallergenic (HA) formula in which the cow milk proteins are hydrolysed. An example of a starter formula is given in Example 2.

(iv) Administration to Toddlers:

1. The *L. reuteri* can also be administered orally to toddlers and young children in the form of in a pharmaceutical or neutriceutical composition, a growing-up milk, a milk based drink, a food supplement, in a baby food, in an enteral nutritional product, a milk based yoghurt, a dessert or pudding, in a biscuit or cereal bar, cereal or in a fruit-based drink.

(v) Administration to Animals:

The *L. reuteri* may also be administered orally to animals alone, or in water, or in the form of a food supplement, a pharmaceutical or nutraceutical composition, or milk or pet food.

Administration with Other Compounds

The *L. reuteri* can be administered alone (pure, or diluted in water or milk, including breast milk, for example) or in a mixture with other compounds (such as dietary supplements, nutritional supplements, medicines, carriers, flavours, digestible or non-digestible ingredients). Vitamins and minerals are examples of typical dietary supplements. In a preferred embodiment, *L. reuteri* is administered in a composition, for example, an infant formula, together with other compounds that enhance the described beneficial effect on the young mammals. Such synergistic compounds may be carriers or a matrix that facilitates the *L. reuteri* delivery to the intestinal tract or they may otherwise enhance the effect of the composition on microbiota of the progeny. Such compounds can be other active compounds that synergistically or separately influence the development of the enteric nervous system in the infant and/or potentiates the effect of the probiotic. An example of such synergistic compounds is maltodextrin. One of the effect of maltodextrin is to provide a carrier for the probiotic, enhancing its effect, and to prevent aggregation.

Other examples of synergistic compounds that may be included in the compositions, especially infant formula, of the invention are prebiotic compounds. A prebiotic is a non-digestible food ingredient that beneficially affects the host by selectively stimulating the growth and/or activity of one or a limited number of bacteria in the colon, and thus improves host health. Such ingredients are non-digestible in the sense that they are not broken down and absorbed in the stomach or small intestine and thus pass intact to the colon, where they are selectively fermented by the beneficial bacteria. Examples of prebiotics include certain oligosaccharides, such as fructo-oligosaccharides (FOS), cow milk oligosaccharides (CMOS) and galacto-oligosaccharides (GOS). A combination of prebiotics may be used such as 90% GOS with 10% short chain fructooligosaccharides such as the product sold under the trade mark Raftilose® or 10% inulin such as the product sold under the trade mark Raftiline®. Other examples of prebiotics that can be used in the context of the present invention include the group of oligosaccharides obtained from milk or other sources, optionally containing sialic acid, fructose, fucose, galactose or mannose. Preferred prebiotics are sialo-oligosaccharides (SOS), fructo-oligosaccharides (FOS), galacto-oligosaccharides (GOS), isomalto-oligosaccharides (IMO), xylo-oligosaccharides (XOS), arabino-xylo oligosaccharides (AXOS), mannan oligosaccharides (MOS), oligosaccharides of soy, glycosylsucrose (GS), lactosucrose (LS), sialyl-lactose (SL), fucosyl-lactose (FL), lacto-N-neotetraose (LNNT), lactoneotetraose (LNT), lactulose (LA), palatinose-oligosaccharides (PAO), malto-oligosaccharides, gums/or hydrolysates thereof, pectins, starches, and/or hydrolysates thereof. An infant formula according to the invention preferably further contains at least one prebiotic in an amount of 0.3 to 10% of the total weight of the dry composition.

In particular, the human milk oligosaccharides, for example sialylated oligosaccharides, described in WO 2012/069416 published on May 31, 2012 may be included in the composition according to the invention. The latter oligosaccharides may act in synergy with the *L. reuteri* of the invention to promote the recovery of C-section induced microbiota dysbiosis.

Other probiotics may be also administered. Preferably, the probiotic may be selected for this purpose from the group consisting of *Bifidobacterium, Lactobacillus, Lactococcus, Enterococcus, Streptococcus, Kluyveromyces, Saccharoymces, Candida*, in particular selected from the group consisting of *Bifidobacterium longum, Bifidobacterium lactis, Bifidobacterium animalis, Bifidobacterium breve, Bifidobacterium infantis, Bifidobacterium adolescentis, Lacto-*

*bacillus acidophilus, Lactobacillus casei, Lactobacillus paracasei, Lactobacillus salivarius, Lactobacillus lactis, Lactobacillus rhamnosus, Lactobacillus johnsonii, Lactobacillus plantarum, Lactobacillus salivarius, Lactococcus lactis, Enterococcus faecium, Saccharomyces cerevisiae, Saccharomyces boulardii* or mixtures thereof, preferably selected from the group consisting of *Bifidobacterium longum* NCC3001 (ATCC BAA-999), *Bifidobacterium longum* NCC2705 (CNCM 1-2618), *Bifidobacterium longum* NCC490 (CNCM 1-2170), *Bifidobacterium lactis* NCC2818 (CNCM 1-3446), *Bifidobacterium breve* strain A, *Lactobacillus paracasei* NCC2461 (CNCM I-2116), *Lactobacillus johnsonii* NCC533 (CNCM 1-1225), *Lactobacillus rhamnosus* GG (ATCC53103), *Lactobacillus rhamnosus* NCC4007 (CGMCC 1.3724), *Enterococcus faecium* SF 68 (NCC2768; NCIMB10415), and mixtures thereof.

The daily doses of carbohydrates, and all other compounds administered with the *L. reuteri* should always comply with the published safety guidelines and regulatory requirements. This is particularly important with respect to the administration to new-born babies, especially those born with low birth weight, very low or extremely low birth weight.

Infant formulas containing the *L. reuteri* may contain a protein source in an amount of not more than 4.0, 3.0 or 2.0 g/100 kcal, preferably 1.8 to 2.0 g/100 kcal. The type of protein is not believed to be critical to the present invention provided that the minimum requirements for essential amino acid content are met and satisfactory growth is ensured although it is preferred that over 50% by weight of the protein source is whey. In one embodiment, the protein content is between 30% and 80% whey proteins. Thus, protein sources based on whey, casein and mixtures thereof may be used as well as protein sources based on soy. As far as whey proteins are concerned, the protein source may be based on acid whey or sweet whey or mixtures thereof and may include alpha-lactalbumin and beta-lactoglobulin in whatever proportions are desired.

The proteins may be intact or hydrolysed or a mixture of intact and hydrolysed proteins. It may be desirable to supply partially hydrolysed proteins (degree of hydrolysis between 2 and 20%), for example for infants believed to be at risk of developing cows' milk allergy. If hydrolysed proteins are required, the hydrolysis process may be carried out as desired and as is known in the art. For example, a whey protein hydrolysate may be prepared by enzymatically hydrolysing the whey fraction in one or more steps. If the whey fraction used as the starting material is substantially lactose free, it is found that the protein suffers much less lysine blockage during the hydrolysis process. This enables the extent of lysine blockage to be reduced from about 15% by weight of total lysine to less than about 10% by weight of lysine; for example about 7% by weight of lysine which greatly improves the nutritional quality of the protein source.

The composition may also comprise a source of carbohydrates and/or a source of fat. The infant formula may contain a source of lipids. The lipid source may be any lipid or fat which is suitable for use in infant formulas. Preferred fat sources include palm olein, milk fat, high oleic sunflower oil and high oleic safflower oil. The essential fatty acids, linoleic and α-linolenic acid may also be added as small amounts of oils containing high quantities of preformed arachidonic acid and docosahexaenoic acid such as fish oils or microbial oils. In total, the fat content is preferably such as to contribute between 30 to 55% of the total energy of the formula. The fat source preferably has a ratio of n-6 to n-3 fatty acids of about 5:1 to about 15:1, for example about 8:1 to about 10:1.

An additional source of carbohydrate may be added to the nutritional composition. It preferably provides about 40% to about 80% of the energy of the nutritional composition. Any suitable carbohydrate may be used, for example sucrose, lactose, glucose, fructose, corn syrup solids, maltodextrin, or a mixture thereof.

Additional dietary fibre may also be added if desired. If added, it preferably comprises up to about 5% of the energy of the nutritional composition. The dietary fibre may be from any suitable origin, including for example soy, pea, oat, pectin, guar gum, acacia gum, fructo-oligosaccharide or a mixture thereof. Suitable vitamins and minerals may be included in the nutritional composition in an amount to meet the appropriate guidelines.

Examples of minerals, vitamins and other nutrients optionally present in the infant formula include vitamin A, vitamin B1, vitamin B2, vitamin B6, vitamin B 12, vitamin E, vitamin K, vitamin C, vitamin D, folic acid, inositol, niacin, biotin, pantothenic acid, choline, calcium, phosphorous, iodine, iron, magnesium, copper, zinc, manganese, chloride, potassium, sodium, selenium, chromium, molybdenum, taurine, and L-carnitine. Minerals are usually added in salt form. The presence and amounts of specific minerals and other vitamins will vary depending on the intended infant population.

The infant formula may optionally contain other substances which may have a beneficial effect such as fibres, lactoferrin, nucleotides, nucleosides, and the like.

One or more essential long chain fatty acids (LC-PUFAs) may be included in the composition. Examples of LC-PUFAs that may be added are docosahexaenoic acid (DHA) and arachidonic acid (AA). The LC-PUFAs may be added at concentrations so that they constitute greater than 0.01% of the fatty acids present in the composition.

One or more food grade emulsifiers may be included in the nutritional composition if desired; for example diacetyl tartaric acid esters of mono- and di- glycerides, lecithin and mono- or di-glycerides or a mixture thereof. Similarly, suitable salts and/or stabilisers may be included. Flavours can be added to the composition.

Administration Period:

The duration of the administration may vary. While positive effects are expected with relatively short duration of administration (for example, daily administration during one to two weeks for newborns), longer durations are believed to provide an enhanced effect, or, at least, to maintain the effect in older infants and toddlers (for example, a duration of three, five, eight, 12, 24 or 36 months). For administration to animals, the corresponding durations apply.

The expectant mother may start to take the *L. reuteri* as soon as she is aware of her pregnancy. However, the administration period may also start before pregnancy starts, for example if the female is trying to become pregnant. Administration may start at any time after the pregnancy starts. It may start relatively late in the pregnancy, preferably at month 3, 4, 5, 6, 7, 8 or 9 of the pregnancy, in the case of human pregnancy, or in corresponding periods for other mammals, or up to one week before the expected delivery date.

The period of administration can be continuous (for example, up to and including lactation up to weaning), or discontinuous. Continuous administration is preferred for a more sustained effect. However, it is speculated that a discontinuous pattern (for example, daily administration during one week per month, or during alternate weeks) can induce positive effects on the progeny.

The administration may cover at least part of the gestation period and at least part of the lactation period if the newborn is fed with mother's milk, or the equivalent period, should the newborn not be fed with mother's milk.

Preferably, the administration period to the expectant mother covers substantially the full length of the gestation period, although this may be less. Similarly, the administration period for the lactating mother preferably covers substantially the full length of the lactation period, although, again, this period may be less.

Preferably, the administration to the mother is by daily intake (to be taken once or twice a day), or weekly intake (to be taken one or twice a week).

The *L. reuteri* may be administered to the infant directly. This is the case particularly if the mother does not breastfeed, or after she discontinues breastfeeding. However, an infant who is being breastfed may also receive the *L. reuteri* by direct administration.

Preferably, the administration to the infant is by daily intake. For example, if the *L. reuteri* is administered as an infant formula, the administration is with each feed, i.e. about four to about six times daily for infants less than one year old, the number of feeds reducing with age.

The administration to the infant, either via breastfeeding, or by direct administration, or both methods, may be continued up until the age of six months or longer. Thus, the *L. reuteri* may be administered during lactation, if lactation takes place, or after partial or full weaning.

Effect of the *L. reuteri* Administration:

The present inventors have surprisingly found that administration of *L. reuteri* to caesarian delivered infants leads, not simply to *L. reuteri* colonization, as one might expect, but to the complete establishment of a "normal" microbiota, characteristic of a vaginally born infant, who has not been exposed to antibiotics or suffered events that are known to disturb the gut microbiota in infants. This has been demonstrated in a clinical study involving the genetic analysis of microbiota from stool samples of the infants (see Example 1).

From these data, it can be established that the administration of *L. reuteri* to young mammals, in particular to infants, treats or prevents microbiota dysbiosis. The microbiota dysbiosis in Example 1 was caused by C-section delivery. In general, microbiota dysbiosis may also be caused by premature birth (C-section or vaginally), exposure to antibiotics in utero or after birth, parenteral feeding, hospitalization, psychological stress, gastrointestinal dysfunctions (digestive disorders, motility disorders, gastrointestinal reflux, slow gastrointestinal transit, oral feeding intolerance, constipation, diarrhea), Hirschsprung's disease, short bowel syndrome, gastrointestinal infection and inflammation affecting the gastrointestinal tract (such as Necrotisis enterocolitis) and obstruction pathologies.

The administration of *L. reuteri* promotes the recovery of a "normal" microbiota population as that seen in infants born by vaginal deliveries. The *L. reuteri* promotes the recovery of C-section induced dysbiosis. In the clinical experiment, detailed in Example 1, the effect of *L. reuteri* administration on the recovery of C-section induced microbiota dysbiosis was evaluated. The inventors compared the evolution of the microbiota composition in infants born by C-section and fed either an infant formula containing *L. reuteri* DSM 17938 or a control formula with similar composition but without the probiotic.

Delivery by C-section induced important changes in the global microbiota profile and taxa levels in the control group, especially 2 weeks after birth, but still detectable at 4 months of age.

FIG. 1 shows a dendogram clustering the four groups according to the phylogenetic similarity of their microbiota profile at both 2 weeks and 4 months of age. At 2 weeks, the groups born via the vaginal route tightly cluster with the group born by C-section and fed the *L reuteri* formula, with a clear separation from the C-section group fed the control formula. At this age the microbiota profile of infants born by C-section and fed the control formula was significantly different from those born by vaginal delivery (Cont C vs Cont V: p=0.009; Cont C vs *L. reuteri* V: p=0.01). In contrast, C-section infants fed with the *L. reuteri* formula had a microbiota profile closer to and not significantly different from the vaginal delivery groups (*L reuteri* C vs Cont V: p=0.332; *L. reuteri* C vs *L. reuteri* V: p=0.682; *L reuteri* C vs Cont C: p=0.013).

The relative abundance at age 2 weeks of the Phylum taxa in the different groups is shown in FIG. 2 and Table 1. The P values of the comparisons between each group and the control vaginal group are displayed in Table 2.

TABLE 1

Median (SEmedian) values of the Phylum taxa relative abundance for each group at 2 weeks of age[1]

| | Ctrl V | Ctrl C | Lreuteri V | Lreuteri C |
|---|---|---|---|---|
| Firmicutes | 49.0 (17.5) | 59.5 (11.7) | 60.3 (11.9) | 58.5 (9.3) |
| Actinobacteria | 44.5 (17.5) | **0.5 (0.3)** | 36.0 (12.3) | 25.4 (13.5) |
| Proteobacteria | 2.5 (1.0) | **27.6 (13.8)** | 2.4 (3.2) | 7.3 (3.8) |
| Bacteroidetes | 0.1 (0.1) | 0.0 (0.0) | 0.0 (0.0) | 0.0 (0.0) |
| Other | 0.0 (0.0) | 0.2 (0.1) | 0.2 (0.2) | 0.1 (0.0) |
| Verrucomicrobia | 0.0 (0.0) | 0.0 (0.0) | 0.0 (0.0) | 0.0 (0.0) |

[1]Values in bold and black indicate for a given group the Phyla that are significantly different from the Control Vaginal group (cf. Table 2).

TABLE 2

P values for each pairwise comparison (Wilcoxon test) of the Phylum taxa median relative abundance at 2 weeks of age[1]

| | Ctrl V vs. Ctrl C | Ctrl V vs. Lreuteri | Ctrl V vs. Lreuteri V C |
|---|---|---|---|
| Firmicutes | 0.315 | 0.905 | 0.314 |
| Actinobacteria | **0.008** | 0.720 | 0.426 |
| Proteobacteria | **0.011** | 0.842 | 0.809 |
| Bacteroidetes | 0.224 | 0.628 | **0.021** |
| Other | 0.631 | 0.093 | 0.377 |
| Verrucomicrobia* | | | |

*no P value derived since almost no infant has Verrucomicrobia

[1]Differences are considered significant at $P < 0.05$.

At two weeks, the relative abundance of Actinobacteria was strongly reduced in infants born by C-section and fed the control formula, whereas the abundance of Proteobacteria was strongly increased in this group. By contrast, the C-section group fed with the *L. reuteri* formula had Actinobacteria and Proteobacteria levels close and not significantly different from the vaginal delivery groups. Of note is the fact that the Actinobacteria phylum contains beneficial micro-organisms such as the genus *Bifidobacterium*, whereas the phylum Proteobacteria includes potentially pathogenic genera such as *Escherichia, Shigella* and *Klebsiella.*

Figure 3:
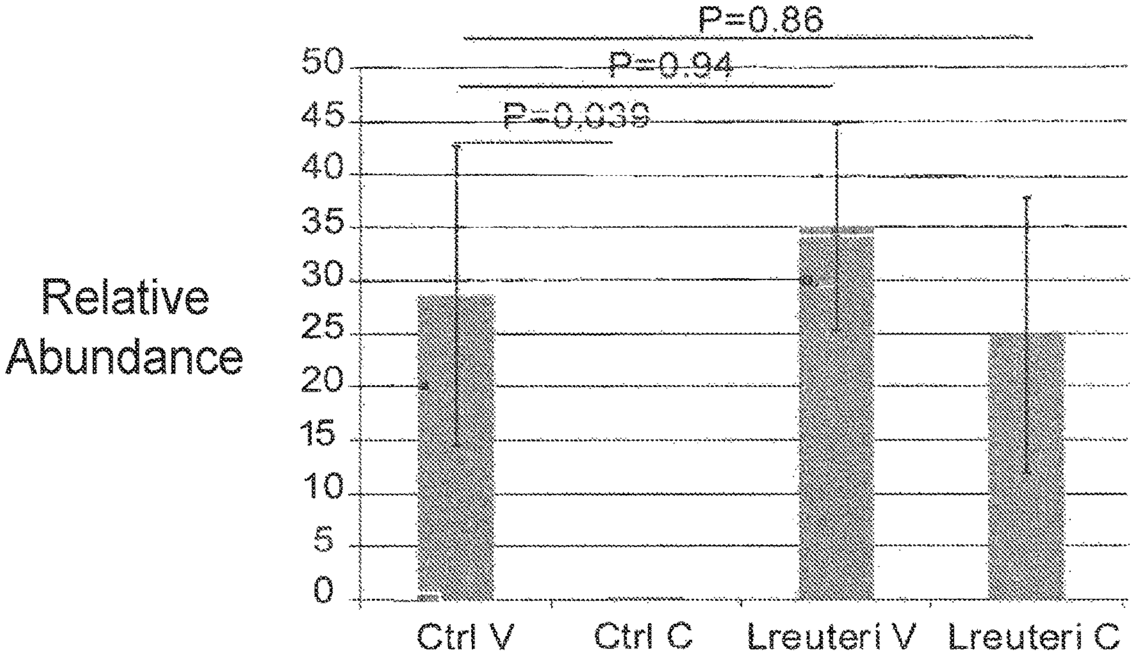
FIG. 3: Relative abundance of *Bifidobacterium* spp. in feces of each experimental group at 2 weeks. Control vaginal (Ctrl V), control cesarean (Ctrl C), *L. reuteri* vaginal (*L. reuteri* V) and *L. reuteri* cesarean (*L. reuteri* C). The error bar indicates the SEmedian. P values for the pairwise comparisons between each group vs. the control vaginal group (Ctrl V) are displayed (Wilcoxon test). Differences are considered significant at $P<0.05$.

*Bifidobacterium* was undetectable in most infants of the C-section, control group. This is illustrated in FIG. 3 which shows the relative abundance of *Bifidobacterium* spp. in each group at 2 weeks of age. *Bifidobacterium* spp. was not detectable in most infants of the control caesarean group. As a consequence, the median value in this group was 0 and significantly lower than the median value of the control group born by vaginal delivery. By contrast, the levels of *Bifidobacterium* spp. in the C-section group fed with the *L. reuteri* formula were close to and not significantly different from the groups born by vaginal delivery.

The potentially harmful genera *Klebsiella* and *Escherichia/Shigella* were far more abundant in the C-section, control group (3.0% and 18.2%, respectively) than in its vaginal-delivery counterpart (0.3% and 5.6%, respectively). Relative abundance of these genera was near vaginal delivery levels in the C-section, *L. reuteri* group (1.2% and 7.4%, respectively).

At 4 months old, the global microbiota profile of each group vs. the control vaginal group was no longer significant (FIG. 1), indicating that, as expected, the effect of C-section on microbiota composition was milder at the older age. Nevertheless, a significant effect of the mode of delivery on the relative abundance of several taxa was still observed in the group fed the control formula. C-section resulted in increased relative abundance of the phylum Firmicutes, of the family Enterococcaceae and of the genera *Enterococcus* and *Coprococcus*, as well as decreased relative abundance of the family Coriobacteriaceae and of the genus Collinsella.

Interestingly, compared to the vaginal delivery infants, no significant differences were observed in the relative abundance of any of the taxa in the C-section group fed with *L. reuteri* supplemented formula.

Thus, *L. reuteri* containing formula induced a shift of the microbiota in C-section babies towards the vaginal delivery profile/levels, with a strong effect observed at two weeks and a complete microbiota recovery at four months.

The *L. reuteri* formula promoted the recovery of the microbiota dysbiosis induced by C-section. Specifically, *L. reuteri* induced an increase in Actinobacteria levels, and a decrease in Proteobacteria levels so that the levels of these phyla were not significantly different from vaginally born infants. This general recovery of microbiota dysbiosis in the C-section infants towards a microbiota strongly resembling that of vaginally-born infants represents significant advantage for maintaining the health of those C-section infants, during infancy, childhood and later in life. Thus, administration of *L. reuteri* may prevent or treat disorders associated with C-section induced microbiota dysbiosis in young mammals. To the inventors knowledge, no oral treatment in the prior art has demonstrated this ability to treat microbiota dysbiosis.

The invention is beneficial to those young mammals that are suffering or are at risk of suffering microbiota dysbiosis. Specifically, populations that may benefit from administration of *L. reuteri* according to the invention are those young mammals up to the age of 3 who:

- have been delivered by cesarean section,
- were exposed to antibiotics in utero during delivery or, once born, were, or, are still being exposed to antibiotics,
- were born prematurely (vaginally or by C-section),
- were or are being fed parenterally,
- experienced or are still experiencing hospitalization or psychological stress,
- suffered or are still suffering from gastrointestinal dysfunctions including digestive disorders, motility disorders, gastrointestinal reflux, slow gastrointestinal transit, oral feeding intolerance, Hirschsprung's disease, and inflammation affecting the gastrointestinal tract, such as Necrotisis enterocolitis, and obstruction pathologies.

Although the invention has been described by way of example, it should be appreciated that variations and modifications may be made without departing from the scope of the invention as defined in the claims. Furthermore, where known equivalents exist to specific features, such equivalents are incorporated as if specifically referred in this specification.

Example 1

Clinical Study

Study Set-Up

A single-center, prospective, randomized, controlled, double-blind clinical trial of two groups in parallel was carried out. Healthy, full-term babies, anticipated to be exclusively formula-fed were enrolled in the study. Infants were enrolled within the 48 hours following birth and were randomly assigned to one of 2 treatment groups:

1. Subjects receiving Starter Formula containing *Lactobacillus reuteri* ($10^8$ cfu of *L. reuteri* per day) from birth to 6 months (n=60).

2. Subjects receiving Starter Formula without *Lactobacillus reuteri* from birth to 6 months (n=60).

Stool samples were collected at 14 days and 4 months of infant age, refrigerated at 4° C. for a maximum of 10 hours after emission and kept frozen at −80° C. until microbiota analysis was carried out.

Fecalmicrobiotaanalysis

Twenty infants in each group were selected to study the fecal microbiota composition. The selection was performed randomly, but with two stratification criteria: gender (10 males and 10 females in each group) and delivery type (10 infants born by vaginal and 10 infants born by caesarean delivery in each group).

Fecal microbiota composition was measured at both time points by pyrosequencing of variable regions of the 16S RNA genes present in the microbial population. DNA was extracted from fecal samples with the Qiacube (QIAgen). Primers were designed as previously proposed [Hamady, M., Walker, J. J., Harris, J. K., N. et al. (2008), Error-correcting barcoded primers for pyrosequencing hundreds of samples in multiplex, *Nat. Methods,* 5:235-237] to amplify the V1 to V3 variable regions of the 16S gene, showing a high taxonomical informative level. Using barcoding techniques, multiplex pyrosequencing was performed. Each sample was characterized by 1500 sequencing reads in average. High quality reads were identified and analyzed using QIIME analytical package [Caporaso, J. G., Kuczynski, J., Stombaugh, J. et al. (2010), QIIME allows analysis of high-throughput community sequencing data, *Nat Methods,* 7(5):335-6]. Reads were grouped into Operational Taxonomic Groups (OTUs) at 97% identity and further classified using the RDP-Classifier with 0.6 confidence level [Wang, Q., Garrity, G. M., Tiedje, J. M. and Cole, J. R. (2007), Naive Bayesian classifier for rapid assignment of rRNA sequences into the new bacterial taxonomy, *Appl. Environ. Microbiol.,* 73:5261-5267].

The statistical analysis of the microbiota data was performed by using the program R 2.14.1 [R Development Core Team. R: A language and environment for statistical computing. R Foundation for Statistical Computing, Vienna, Austria. ISBN 3-900051-07-0, URL http://www.R-project.org/]. The effects of gender and delivery type were tested by using a NP MANOVA (Non-Parametric Multivariate ANalysis Of Variance) at each taxonomic level and 16S region with gender or delivery type as one of the explanatory variables.

No significant effect of gender was observed and data from males and females were further analysed together. By contrast, the mode of delivery strongly modulated both the global microbiota profile and the taxa relative abundance. To further explore the effect of the mode of delivery, data were analysed by comparing the following 4 groups: Vaginal delivery fed control (control vaginal) or *L. reuteri* (*L. reuteri* vaginal) formula and C-section delivery fed control (control caesarean) or *L. reuteri* (*L. reuteri* cesarean) formula. NP MANOVA was used to analyze the multivariate Euclidean distance data between two groups. The Wilcoxon signed-rank test was used for pairwise comparison of the relative abundance of each individual taxa.

Example 2

An example of the composition of an infant formula for use according to the present invention is given below. This composition is given by way of illustration only. The protein source is a mixture of 60% MSWP28 and 40% casein.

| Nutrient | per 100 kcal | per liter |
|---|---|---|
| Energy (kcal) | 100 | 670 |
| Protein (g) | 1.83 | 12.3 |
| Fat (g) | 5.3 | 35.7 |
| Linoleic acid (g) | 0.79 | 5.3 |
| α-Linolenic acid (mg) | 101 | 675 |
| Lactose (g) | 11.2 | 74.7 |
| Prebiotic (100% GOS) (g) | 0.64 | 4.3 |
| Minerals (g) | 0.37 | 2.5 |
| Na (mg) | 23 | 150 |
| K (mg) | 89 | 590 |
| Cl (mg) | 64 | 430 |
| Ca (mg) | 62 | 410 |
| P (mg) | 31 | 210 |
| Mg (mg) | 7 | 50 |
| Mn (μg) | 8 | 50 |
| Se (μg) | 2 | 13 |
| Vitamin A (μg RE) | 105 | 700 |
| Vitamin D (μg) | 1.5 | 10 |
| Vitamin E (mg TE) | 0.8 | 5.4 |
| Vitamin K1 (μg) | 8 | 54 |
| Vitamin C (mg) | 10 | 67 |
| Vitamin B1 (mg) | 0.07 | 0.47 |
| Vitamin B2 (mg) | 0.15 | 1.0 |
| Niacin (mg) | 1 | 6.7 |
| Vitamin B6 (mg) | 0.075 | 0.50 |
| Folic acid (μg) | 9 | 60 |
| Pantothenic acid (mg) | 0.45 | 3 |
| Vitamin B12 (μg) | 0.3 | 2 |
| Biotin (μg) | 2.2 | 15 |
| Choline (mg) | 10 | 67 |
| Fe (mg) | 1.2 | 8 |
| I (μg) | 15 | 100 |
| Cu (mg) | 0.06 | 0.4 |
| Zn (mg) | 0.75 | 5 |
| *L. reuteri* DSM 17938 | $2 \times 10^7$ cfu/g of powder | |

The invention claimed is:

1. A method for treatment or reducing a risk of one or more disorders selected from the group consisting of insulin resistance, type 2 diabetes, peripheral and central adiposity, and obesity, wherein the one or more disorders are associated with microbiota dysbiosis occurring in a young human aged up to three years of age, the one or more disorders occurring in the young human or later in the life of the young human, the method comprising administering *Lactobacillus reuteri* to the young human, wherein the young human is suffering from the microbiota dysbiosis, and the administering is effective to treat the microbiota dysbiosis.

2. The method according to claim 1, wherein the *Lactobacillus reuteri* is administered in a combination with one or more additional probiotics.

3. The method according to claim 2, wherein the one or more additional probiotics comprise a *Bifidobacterium longum.*

4. The method according to claim 1, wherein the young human is selected from the group consisting of a human fetus, a pre-term infant, a term-born infant and a toddler.

5. The method according to claim 1, wherein the young human is a fetus, and the *Lactobacillus reuteri* is indirectly administered to the fetus via administration to the expectant mother.

6. The method according to claim 1, wherein the *Lactobacillus reuteri* is administered (i) directly to the young human or (ii) indirectly to the young human via administration to the lactating mother.

7. The method according to claim 1, wherein the *Lactobacillus reuteri* is administered to the young human for a period of at least one week.

8. The method according to claim 1, wherein the *Lactobacillus reuteri* is administered directly to the young human in at least one form selected from the group consisting of a pure form, diluted in water or breast milk, in a food supplement, in a milk fortifier, in any milk support used during trophic feeding, in a growing-up milk, in a milk based drink, in an infant formula, in a pharmaceutical composition, in a nutriceutical composition, in a baby food, in an enteral nutritional product, in a milk-based yoghurt, in a dessert, in a pudding, in a biscuit, in a cereal bar, in a cereal and in a fruit-based drink.

9. The method according to claim 1, wherein the young human is selected from the group consisting of a fetus with an expectant mother and a breast-fed infant with a lactating mother, and the administration to the young human is via oral administration to the expectant mother or the lactating mother.

10. The method according to claim 1, wherein the young human is selected from the group consisting of an infant and a toddler, and the *Lactobacillus reuteri* is administered to the infant or the toddler as a daily dose of $1\times10^3$ to $1\times10^{12}$ cfu (cfu=colony forming unit).

11. The method according to claim 1, wherein the young human is selected from the group consisting of a fetus with an expectant mother, a breast-fed infant with a lactating mother, and an infant, and the *Lactobacillus reuteri* is administered to the expectant mother, the lactating mother, or the infant as a composition comprising between $1\times10^3$ and $1\times10^{12}$ cfu/g of dry composition.

12. The method according to claim 11, wherein the composition comprises further ingredients.

13. The method according to claim 1, wherein the one or more additional probiotics are selected from the group consisting of *Bifidobacterium longum* BB536 (ATCC BAA-999), *Lactobacillus rhamnosus* (CGMCC 1.3724), *Bifidobacterium lactis* (NCC2818) and mixtures thereof.

14. The method according to claim 1, wherein the *Lactobacillus reuteri* is *Lactobacillus reuteri* DSM 17938.

15. The method according to claim 1, wherein the *Lactobacillus reuteri* is administered to the young human as a daily dose of $1\times10^3$ to $1\times10^{12}$ cfu (cfu=colony forming unit).

* * * * *